(12) United States Patent
Dong et al.

(10) Patent No.: US 11,162,876 B2
(45) Date of Patent: Nov. 2, 2021

(54) LONG-TERM IN-SITU SAMPLING AND ANALYSIS DEVICE FOR SEDIMENT PORE WATER AND METHOD THEREOF

(71) Applicant: Guangzhou Marine Geological Survey, Guangzhou (CN)

(72) Inventors: Yifei Dong, Guangzhou (CN); Qianyong Liang, Guangzhou (CN); Jiawang Chen, Guangzhou (CN); Ziqiang Ren, Guangzhou (CN); Chao Zhong, Guangzhou (CN); Xuemin Wu, Guangzhou (CN)

(73) Assignee: GUANGZHOU MARINE GEOLOGICAL SURVEY, Guangzhou (CN)

( * ) Notice: Subject to any disclaimer, the term of this patent is extended or adjusted under 35 U.S.C. 154(b) by 210 days.

(21) Appl. No.: 16/506,082

(22) Filed: Jul. 9, 2019

(65) Prior Publication Data

US 2020/0011768 A1 Jan. 9, 2020

(30) Foreign Application Priority Data

Jul. 9, 2018 (CN) .......................... 201810747295.7

(51) Int. Cl.
| | | |
|---|---|---|
| *G01N 1/10* | (2006.01) | |
| *F04B 43/12* | (2006.01) | |
| *G01D 21/02* | (2006.01) | |
| *G01L 11/00* | (2006.01) | |
| *G01N 33/18* | (2006.01) | |

(52) U.S. Cl.
CPC ............... *G01N 1/10* (2013.01); *F04B 43/12* (2013.01); *G01D 21/02* (2013.01); *G01L 11/00* (2013.01); *G01N 33/18* (2013.01)

(58) Field of Classification Search
CPC ............ G01N 1/10; G01N 33/18; G01N 1/14; G01N 2001/1418; G01N 1/16; G01N 1/18; G01N 2001/002; G01N 33/1886; F04B 43/12; G01D 21/02
USPC ........ 73/38, 863.01, 863.23, 863.31, 864.34, 73/864.73, 864.74, 864.81
See application file for complete search history.

(56) References Cited

U.S. PATENT DOCUMENTS

| | | | | |
|---|---|---|---|---|
| 8,051,727 B1 * | 11/2011 | Murphy | ................... | G01N 1/10 73/864.74 |
| 2010/0064825 A1 * | 3/2010 | Bell | ..................... | H01J 49/0436 73/863.83 |

FOREIGN PATENT DOCUMENTS

CN 105953971 A 9/2016

* cited by examiner

*Primary Examiner* — Robert R Raevis
(74) *Attorney, Agent, or Firm* — Muncy, Geissler, Olds & Lowe, P.C.

(57) ABSTRACT

The present application discloses a long-term, in-situ sampling and analysis device for sediment pore water and a method thereof. The long-term in-situ sampling and analysis device for sediment pore water includes a bracket, a probe, an elevator, a diverting device, a first water storage device, and a second water storage device, a peristaltic pump, a dissolved gas of sediment pore water analysis device and an in-situ environment measurement device. The present application can collect and store the sediment pore water in an in-situ, long-term and time-phased manner, and in low measuring error level.

10 Claims, 4 Drawing Sheets

LONG-TERM IN-SITU SAMPLING AND ANALYSIS DEVICE FOR SEDIMENT PORE WATER AND METHOD THEREOF

CROSS-REFERENCE TO RELATED APPLICATION

This application is based upon and claims the benefit of priority of the prior Chinese Patent Application No. 201810747295.7, filed on Jul. 9, 2018, the entire contents of which are incorporated herein by reference.

TECHNICAL FIELD

The present application relates to the technical field of seabed sediment pore water collection, and in particular to a long-term in-situ sampling and analysis device for sediment pore water and a method thereof.

BACKGROUND

Pore water refers to groundwater that is mainly present in the pores between the loose sediment particles. The sediment pore water in the superficial sediments of the seabed retains a lot of useful information, such as the abnormalities of $CH_4$, $H_2S$ and other gases, the distribution characteristics of $Cl^-$, $SO_4^{2-}$ and other ions. The methane leakage flux of seabed is measured through these factors, which provides fast and efficient geochemistry evidence for natural gas hydrate (NGH) resource exploration and environmental assessments.

However, the NGH production test will inevitably affect the occurrence of methane in the NGH reservoir. Under the methane oxidation of microorganisms, the geochemical properties in sediment pore water will quickly respond to the changes of methane flux and its upward migration mode. Therefore, the geochemical characteristics of sediment pore water can also be used to evaluate the changes in carbon cycle, in elemental material balance, as well as in seabed oxygen level before and after the NGH production test. All the changes above can provide direct evidence to assess the environmental impacts of NGH production test.

Currently, there are two main types of sediment pore water sampling and analysis devices. First, the sediment sample is collected by a gravity sampler onto the scientific research ship and after that the pore water in sediment is extracted or squeezed in the laboratory. Due to the drastic changes in temperature and pressure conditions, physical and chemical variation in sediment pore water such as gas escaping and constituent oxidating may occur, which can lead to significant measuring error. Secondly, only the sediment pore water in a certain period, which is a piece of instantaneous data, can be acquired by present in-situ sediment pore water extraction devices. It is unable to collect and store in-situ, long-term and time-phased sediment pore water.

SUMMARY

In order to overcome the deficiencies of the prior art, the object of the present application is to provide a long-term, in-situ sampling and analysis device for sediment pore water and a method thereof, which can simultaneously solve the problems that the experimental result has significant errors and the sediment pore water cannot be collected and stored in an in-situ, long-term and time-phased manner.

In order to achieve the above object, the technical solution adopted by the present application is as follows:

A long-term in-situ sampling and analysis device for sediment pore water, comprising a bracket, a probe, an elevator, a diverting device, a first water storage device, a second water storage device, a peristaltic pump, a dissolved gas of sediment pore water analysis device, and an in-situ environment measurement device, wherein the elevator is fixed to the bracket, the elevator is provided with a slide rail, the probe is connected with a slider, the probe is connected with the elevator by a cooperation of the slider and the slide rail, a motor is arranged at the top of the elevator, and the motor drives the slider to slide along the length of the slide rail by a drive assembly; the diverting device is disposed above the probe and fixed to the bracket; the first water storage device and the diverting device are connected by a first pipe; the second water storage device is disposed at the top of the probe and connected to the probe through a second pipe; the peristaltic pump is respectively connected to the second water storage device and the diverting device through a flexible connecting member; and the dissolved gas of sediment pore water analysis device and the in-situ environment measurement device are respectively connected to the diverting device through a third pipe.

Preferably, the long-term in-situ sampling and analysis device for sediment pore water further comprises a central control system, wherein the motor of the elevator, the peristaltic pump, the dissolved gas of sediment pore water analysis device and the in-situ environment measurement device are electrically connected to the central control system, the central control system is used for controlling the working sates of the motor, the peristaltic pump, the dissolved gas of sediment pore water analysis device and the in-situ environment measurement device, so that the probe is inserted into superficial sediment at a predetermined time and/or time interval, and the sediment pore water in the probe is sequentially extracted by the peristaltic pump through the second water storage device and the diverting device into the first water storage device, the dissolved gas of sediment pore water analysis device, and the in-situ environment measurement device.

Preferably, the long-term in-situ sampling and analysis device for sediment pore water further comprises a releaser, an anchor chain and a weight anchor block, wherein the releaser is disposed outside the bracket and fixed to the bracket; the weight anchor block is disposed under the releaser and detachably connected to the releaser through the anchor chain; an upper part of the bracket is wrapped with a buoyant material; and the releaser is configured to receive a recovery control signal sent by a survey vessel or platform located on water surface, and release the weight anchor block according to the recovery control signal.

Preferably, the long-term in-situ sampling and analysis device for sediment pore water further comprises a central control system and a hydroacoustic communication device, wherein the hydroacoustic communication device, the motor of the elevator, the peristaltic pump, the dissolved gas of sediment pore water analysis device, and the in-situ environment measurement device are electrically connected to the central control system; and the hydroacoustic communication device is configured to send data of the dissolved gas of sediment pore water analysis device and the in-situ environment measurement device to the survey vessel or platform.

Preferably, the first water storage device is composed of a plurality of first water storage tanks, and the plurality of first water storage tanks is distributed around the circumference of the diverting device; and the second water storage device is composed of a plurality of second water storage devices, and the plurality of the second water storage tanks is respectively connected to the probe through the second pipe.

Preferably, the probe is composed of five parts, and the five parts respectively extract sediment pore water at five layers; and the second water storage device is composed of five second water storage tanks, and the five second water storage tanks are connected to the five parts of the probe by the second pipe, respectively.

Preferably, a battery compartment is further included, the battery compartment being fixedly coupled to the bracket.

A long-term in-situ sampling and analysis method for sediment pore water, comprising the steps of:

Step 1: Collection of sediment pore water, comprising inserting a probe into superficial sediment, and using a negative pressure method to extract the sediment pore water: starting up a peristaltic pump motor, forming a negative pressure in a second water storage device to cause a spring inside the second water storage device to be compressed, and forming a negative pressure by a spring force to extract the sediment pore water;

Step 2: Storage and analysis of sediment pore water, comprising distributing the sediment pore water acquired at different time periods from different sedimentary layers to the first water storage tank for pressure-keeping storage, and after a long-term in-situ sampling and analysis device for sediment pore water is recovered, analyzing and testing the stored sediment pore water in the laboratory to obtain the abnormality of $Cl^-$ and $SO_4^{2-}$ ions and its distribution characteristics;

Step 3: In-situ measurement of sediment pore water, comprising using a dissolved gas of sediment pore water analysis device to test in-situ $CH_4$ and $CO_2$ gas contents in the air at the top of the collected sediment pore water and the carbon isotope ratio in the gas; and using an in-situ environment measurement device to collect environmental parameters of a sediment pore water collecting station, including temperature, salinity, pressure and dissolved oxygen, thereby providing basic environmental data for sediment pore water characterization.

Preferably, after step 3, the following steps are further included:

Step 4: Underwater communication of data, comprising sending the collected data back through a hydroacoustic communication device to a survey vessel or platform on water surface for researchers to obtain data.

Preferably, after step four, the following steps are further included:

Step 5: Recovery of the long-term in-situ sampling and analysis device for sediment pore water, comprising during launching, causing the long-term in-situ sampling and analysis device for sediment pore water to sit on the seabed relying on an underwater negative buoyancy provided by the weight of a weight anchor block; during recovery, receiving by a releaser a recovery control signal sent by the survey vessel or platform on the water surface, and releasing the weight anchor block according to the recovery control signal; and after releasing the weight anchor block, completing the come-up and recovery of the long-term in-situ sampling and analysis device for sediment pore water using an underwater positive buoyancy provided by a buoyant material.

Compared with the prior art, the beneficial effects of the present application are:

The long-term in-situ sampling and analysis device for sediment pore water and the method thereof, according to the present application, can continuously collect sediment pore water in superficial sediments of the same station in the deep sea for a long period of time, store the sediment pore water in a time-phased and pressure-keeping manner for laboratory analysis after recovery, and measure geochemical information such as ion content in the sediment pore water; and at the same time, can perform rapid and in-situ analysis on the gas content characteristics in the sediment pore water and send the data back to a survey vessel or platform on water surface through a hydroacoustic communication machine.

In the FIG.: 1-bracket; 2-probe; 3-elevator; 4-diverting device; 5-first water storage device; 6-second water storage device; 61-tank; 62-inlet pipe; 63-piston; 64-temporary water storage chamber; 65-outlet pipe; 66-spring; 7-peristaltic pump; 8-dissolved gas of sediment pore water analysis device; 9-in-situ environment measurement device; 10-motor; 11-hose; 12-releaser; 13-anchor chain; 14-weight anchor block; 15-buoyant material; 16-battery compartment.

DETAILED DESCRIPTION

Figure 1:
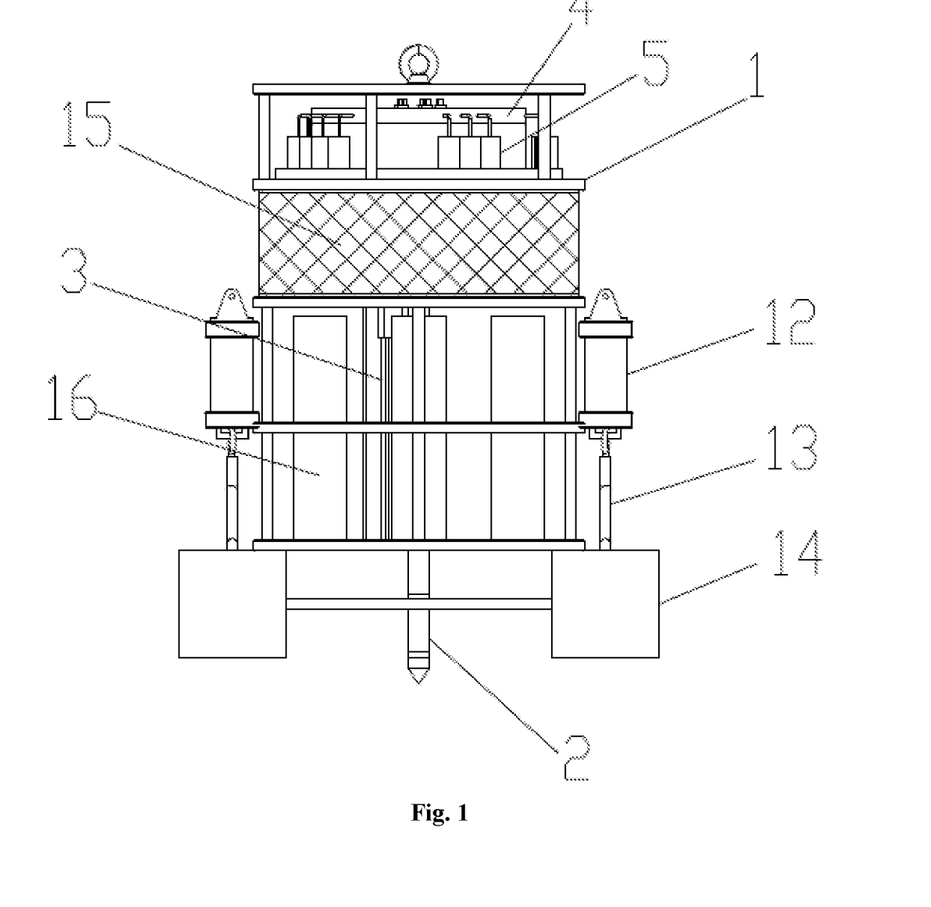
FIG. 1 is a schematic view showing the external overall structure of a long-term in-situ sampling and analysis device for sediment pore water according to the present application.
Figure 2:
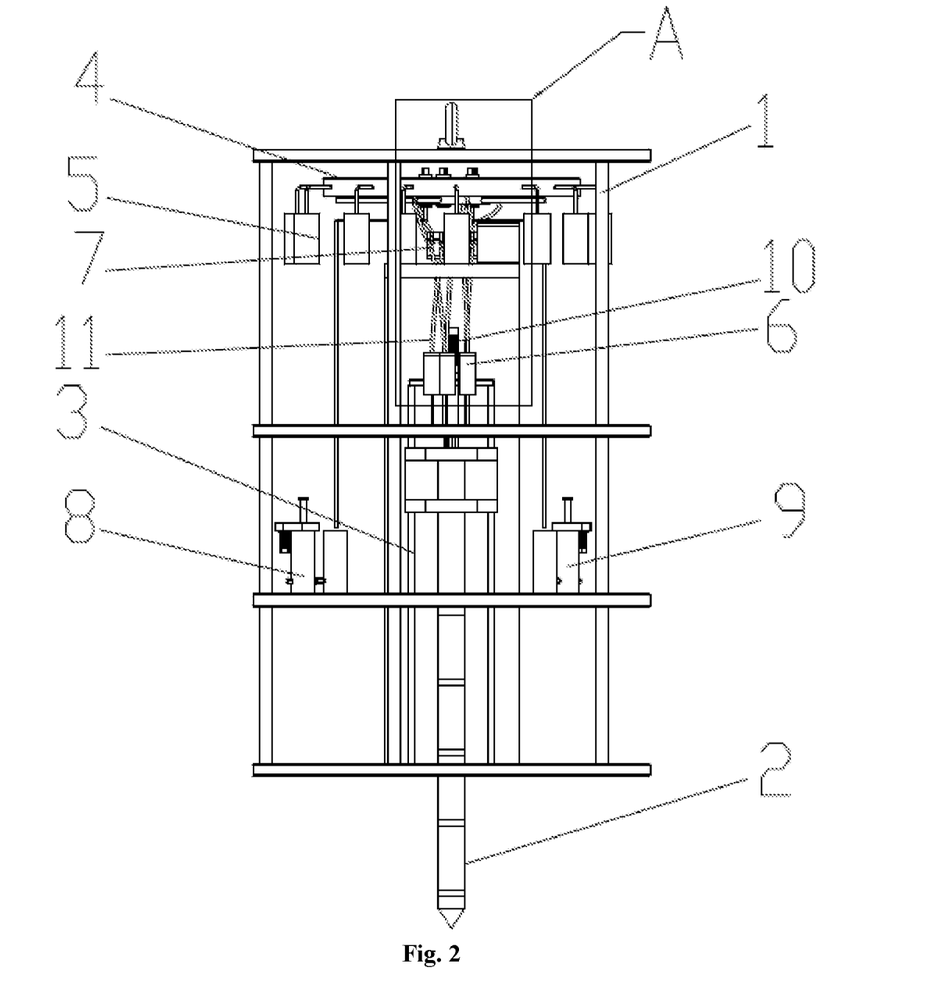
FIG. 2 is a schematic view of the internal structure of FIG. 1.
Figure 3:
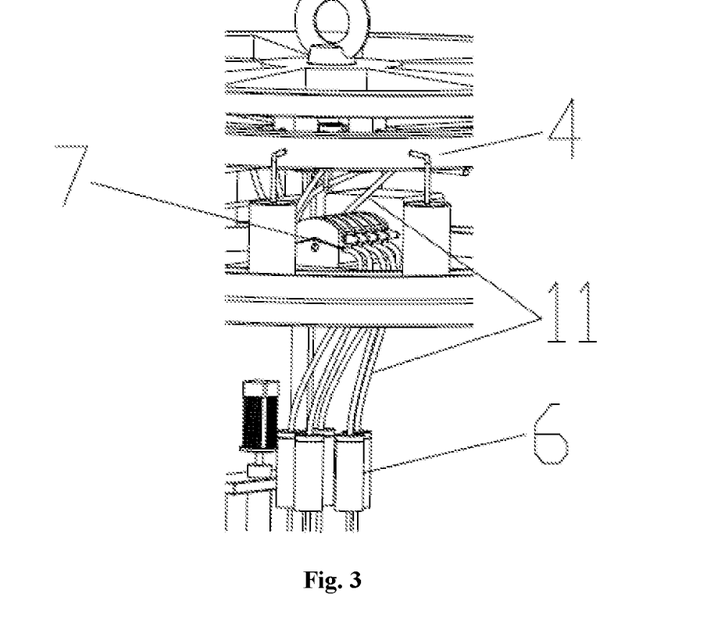
FIG. 3 is an enlarged schematic view of a portion A in FIG. 2.

Hereinafter, the present application will be further described with reference to the accompanying drawings and specific embodiments. As shown in FIGS. 1 to 3, a long-term in-situ sampling and analysis device for sediment pore water according to the present application includes a bracket 1, a probe 2, an elevator 3 a diverting device 4, a first water storage device 5, a second water storage device 6, a peristaltic pump 7, a dissolved gas of sediment pore water analysis device 8, and an in-situ environment measurement device 9. The elevator 3 is fixed to the bracket 1. The elevator 3 is provided with a slide rail. The probe 2 is connected with a slider. The slider is located at an upper outer sidewall of the probe. The probe 2 and the elevator 3 are connected through a cooperation of the slider and the slide rail. The top of the elevator 3 is connected with a motor 10. The motor drives the slider to slide along the length of the slide rail through a drive assembly. Here, the drive assembly can be a gear set or a pulley block. The drive assembly is connected to the probe or the slider. Thus, the motor 10 drives the elevator to lift by the drive assembly, thereby driving the probe 2 to lift.

The diverting device 4 is disposed above the probe 2 and fixed to the bracket 1. The first water storage device 5 is connected to the diverting device 4 through a first pipe. The second water storage device 6 is disposed at the top of the probe 2 and connected to the probe 2 through a second pipe. The peristaltic pump 7 is connected to the second water storage device 6 and the diverting device 4 through a flexible connecting member, respectively. In the embodiment of FIGS. 1 to 3, the flexible connecting member is a hose 11. The dissolved gas of sediment pore water analysis device 8 and the in-situ environment measurement device 9 are respectively connected to the diverting device 4 through a third pipe.

Thus, the probe 2 is inserted into seabed superficial sediment using the elevator 3. The peristaltic pump 7 is turned on. The peristaltic pump 7 causes a negative pressure to be formed inside the second water storage device, so that a spring inside the second water storage device is compressed (see FIG. 4). When the peristaltic pump is turned off, the spring is returned to its original state. A spring force causes a negative pressure to be formed inside the second water storage device, thereby extracting the sediment pore water. Since the second water storage device 6 is disposed at the top of the probe 2, under the action of the peristaltic pump 7, the sediment pore water extracted by the second water storage device 6 moves upward and enters the diverting device 4. On one hand, the diverting device 4 will distribute a portion of the sediment pore water to the first water storage device 5 for long-term storage. On the other hand, the diverting device 4 distributes another portion of the sediment pore water to the dissolved gas of sediment pore water analysis device 8 and the in-situ environment measurement device 9 for analysis and measurement.

Figure 4:
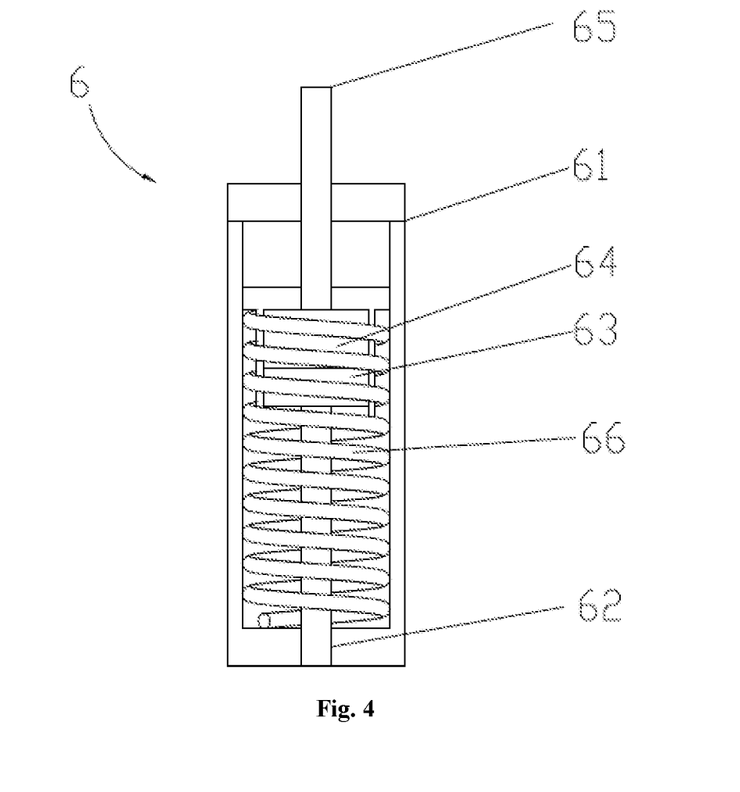
FIG. 4 is a schematic view showing the internal structure of a second water storage device of FIG. 2.

It should be noted that, as shown in FIG. 4, the second water storage device 6 is composed of five second water storage tanks (see FIG. 2). The structure of each second water storage tank includes a tank body 61 and an inlet pipe 62, a piston 63, a temporary water storage chamber 64, an outlet pipe 65 and a spring 66 disposed inside the tank body 61. One end of the inlet pipe 62 passes through the bottom of the tank body 61 and is fixed to the bottom of the tank body 61. The other end is connected to the piston 63. A through hole is provided in the middle of the piston 63. The through hole of the piston 63 corresponds to a through hole of the inlet pipe 62. The piston 63 is disposed in the temporary water storage chamber 64. The temporary water storage chamber 64 is movable up and down with respect to the piston 63 outside the piston 63. One end of the outlet pipe 65 communicates with the temporary water storage chamber 64 and is fixed to the top of the temporary water storage chamber 64. The other end passes through the top of the tank body 61 and is connected with the peristaltic pump 7. The spring 66 is sleeved on an outer wall of the inlet pipe 62 and the temporary water storage chamber. 64. An upper end of the spring 66 is fixed to the top of the temporary water storage chamber 64.

Thus, when the peristaltic pump 7 starts to operate, the sediment pore water stored in the temporary water storage chamber 64 is discharged first, the pressure is lowered, a negative pressure is formed, and the spring 66 is compressed. The temporary water storage chamber 64 moves downward outside the piston 63. The cavity of the temporary water storage chamber 64 becomes small. When the peristaltic pump 7 stops working, the spring 66 is restored to its original state. The cavity of the temporary water storage chamber 64 tends to become large. The internal pressure of the cavity of the temporary water storage chamber 64 is low. The sediment pore water enters the temporary water storage chamber from the inlet pipe. With this circulation, sediment pore water can be extracted.

In the embodiments shown in FIGS. 1 to 3, the long-term in-situ sampling and analysis device for sediment pore water further includes a central control system. The motor 10 of the elevator 3, the peristaltic pump 7, the dissolved gas of sediment pore water analysis device 8 and the in-situ environment measurement device 9 are electrically connected to the central control system. The central control system is used for controlling the working states of the motor 10, the peristaltic pump 7, the dissolved gas of sediment pore water analysis device 8, and the in-situ environment measurement device 9 so that the probe 2 is inserted into the superficial sediment at a predetermined time and/or time interval. The sediment pore water in the probe 2 is extracted by the peristaltic pump 7 sequentially through the second water storage device 6 and the diverting device 4 into the first water storage device 5, the dissolved gas of sediment pore water analysis device 8, and the in-situ environment measurement device 9. In the embodiments shown in FIGS. 1 to 3, as shown in FIG. 1, the sediment pore water long-term in-situ sampling and analysis device further includes a releaser 12, an anchor chain 13 and a weight anchor block 14. The releaser 12 is disposed outside the bracket 1 and fixed to the bracket 1. The weight anchor block 14 is disposed under the releaser 12 and is detachably connected to the releaser 12 through the anchor chain 13. An upper part of the bracket 1 is wrapped with a buoyant material 15. The releaser 12 is configured to receive a recovery control signal sent by a survey vessel or platform located on water surface, and release the weight anchor block 14 according to the recovery control signal. The releaser 12 of the present embodiment can be selected from the IXBLUE, France; the specification and model: the acoustic releaser of the Oceano 2500 S-Universal, which has a wireless communication module that can directly communicate with the surface survey vessel or platform.

In the embodiments shown in FIGS. 1 to 3, the long-term in-situ sampling and analysis device for sediment pore water further includes a central control system and a hydroacoustic communication device (not shown). The hydroacoustic communication device, the releaser 12, the motor 10 of the elevator 3, the peristaltic pump 7, the dissolved gas of sediment pore water analysis device 8 and the in-situ environment measurement device 9 are all electrically connected to the central control system. The hydroacoustic communication device is used for sending the data of the dissolved gas of sediment pore water analysis device and the in-situ environment measurement device to the survey vessel or platform.

Thus, when it is necessary to collect sediment pore water, the long-term in-situ sampling and analysis device for sediment pore water with the weight anchor block 14 is first launched into the seabed. The weight of the weight anchor block 14 provides an underwater negative buoyancy. Since the negative buoyancy provided by the weight anchor block in the water is greater than a positive buoyancy provided by the buoyant material, the long-term in-situ sampling and analysis device for sediment pore water is seated on the seabed to collect sediment pore water. When the collection is completed, that is, when the recovery device 12 receives the recovery control signal from the water surface during releasing, the releaser 12 releases the weight anchor block 14. Then the long-term in-situ sampling and analysis device for sediment pore water after the weight anchor block is released utilizes the underwater positive buoyancy provided by the buoyant material 15 wrapped in the upper part of the bracket 1 to complete come-up and recovery.

In the embodiments shown in FIGS. 1 to 3, the first water storage device 5 is composed of a plurality of first water storage tanks. The plurality of first water storage tanks is distributed around the circumference of the diverting device 4. The second water storage device 6 is composed of a plurality of second water storage tanks. The plurality of the second water storage tanks is respectively connected to the probe through the second pipe. In this way, the diverting device can simultaneously distribute the extracted sediment pore water to the plurality of first water storage tanks. The plurality of second water storage tanks can also be used to simultaneously extract sediment pore water at a plurality of different layers. As a result, the work efficiency is increased and subsequent laboratory research is facilitated.

In the embodiments shown in FIGS. 1 to 3, the probe 2 is composed of five parts. The five parts respectively extract sediment pore water at five layers. The second water storage device 6 is composed of five second water storage tanks. The five second water storage tanks are respectively connected to the five parts of the probe through the second pipe. In this way, the five second water storage tanks respectively extract sediment pore water at five layers for subsequent study of the sediment pore water at each layer of the seabed. Such an arrangement is also convenient for subsequent research.

It should be noted that there are five second water storage tanks, the five second water storage tanks respectively extract sediment pore water at five different layers, and the five second water storage tanks are connected to the peristaltic pump passed through five hoses. The peristaltic pump 7 is connected to the diverting device by means of five hoses. There is a plurality of first water storage tanks. Each of the first water storage tanks is provided with five compartments respectively storing sediment pore water at five layers. The five compartments for sediment pore water at five layers are respectively connected to the five hoses of the diverting device through five first pipes, so that the five compartments correspond to the five second water storage tanks. Therefore, the five compartments respectively store the sediment pore water of the five parts of the probe extracted by the five second water storage tanks.

The long-term in-situ sampling and analysis device for sediment pore water described in the embodiments shown in FIGS. 1 to 3 further includes a battery compartment 16. The battery compartment 16 is fixedly coupled to the bracket 1. The battery compartment 16 is used to provide a source of electrical power to the entire device.

It should be noted that the battery compartment is provided with a large-capacity lithium battery pack, and a power supply system composed of the battery compartment and the lithium battery pack provides the required power for the central control system, thereby satisfying the long-term measurement of the long-term in-situ sampling and analysis device for sediment pore water.

Therefore, as a whole, the long-term in-situ sampling and analysis device for sediment pore water consists of a central control system, a collection system, and an auxiliary system.

The central control system consists of two parts. First, the control system is responsible for controlling data collection timing and storing data. Second, the power supply system uses the deep-sea large-capacity lithium battery pack to provide the required power for the entire device, which should meet the long-term measurement demand.

The collection system includes a sediment pore water collection system portion and an in-situ measurement system portion. The sediment pore water collection system is used for collecting sediment pore water and storing samples. The sediment pore water collection system is the core part of the whole device. The probe is inserted into the superficial sediment. A negative pressure method is adopted to extract the sediment pore water. The peristaltic pump motor is turned on. A negative pressure is formed to cause the spring to be compressed. A spring force forms a negative pressure to extract the sediment pore water. The device can extract sediment pore water at different sedimentary layers, and store the sediment pore water samples acquired at different time periods and different sedimentary layers in a bottle-by-bottle and pressure-keeping manner. After the equipment is recovered, the stored sediment pore water samples can be stored in the laboratory for analytical tests to obtain the anomalies of $Cl^-$ and $SO_4^{2-}$ ions and their distribution characteristics. When the sediment pore water is extracted, the probe is inserted into the seabed sediment to a depth of about 0.5 to 1 m through controlling the elevator to be lifted by a small motor to extract sediment pore water at five different layers respectively, and then recovered after the extraction. The insertion depth is based on actual needs. For example, if being inserted by 0.5 m, the five layers are 0-0.1 m, 0.1-0.2 m, 0.2-0.3 m, 0.3-0.4 m and 0.4-0.5 m respectively. If being inserted by 1.0 m, the five layers are 0-0.2 m, 0.2-0.4 m, 0.4-0.6 m, 0.6-0.8 m and 0.8-1.0 m respectively.

The in-situ measurement system is used to measure the gas content in the air of the sediment pore water, the carbon isotope ratio in the gas, and the seabed environmental parameters of the sediment pore water collection station. The in-situ measurement system is further divided into two parts, one is the dissolved gas of sediment pore water measurement device which can test the in-situ gas content (mainly $CH_4$, $CO_2$) in the headspace air of the sediment pore water and the carbon isotope ratio in the gas using a gas analysis device (for example, model: American Picarro G2201-i isotope analysis device); the other is the "in-situ environment measurement device" which collects seabed environmental parameters of the sediment pore water collection station through a seawater chemical sensor such as CTD(Conductance, Temperature and Depth Sensor) (for example, the model: US Seabird 16 Plus) V2 or Seabird 37), including temperature, salinity, pressure, dissolved oxygen, etc., to provide basic environmental data for sediment pore water characteristics analysis.

The auxiliary system comprises a recovery system and a hydroacoustic communication system. The recovery system is used for recovering the gas collection device. The hydroacoustic communication system is used for sending the collected data back to the water surface. The recovery system guarantees the smooth recovery of the entire long-term in-situ sampling and analysis device for sediment pore water. A chain structure or cable is used to connect the acoustic releaser and the weight anchor block. When launched, an underwater negative buoyancy is provided by the weight of the weight anchor block to cause the collection device to be seated on the seabed. During recovery, an acoustic releaser deck unit is used to send instructions on the survey vessel, so that the releaser discards the weight anchor block and completes come-up and recovery using the underwater positive buoyancy provided by the buoyant material or a float ball.

The hydroacoustic communication system of data can send the collected data back to the survey vessel or platform on the water surface through a hydroacoustic communication machine or an acoustic communication module of the releaser. The researcher can obtain the data quickly and in real time, thus providing references and recommendations for subsequent working.

Figure 5:
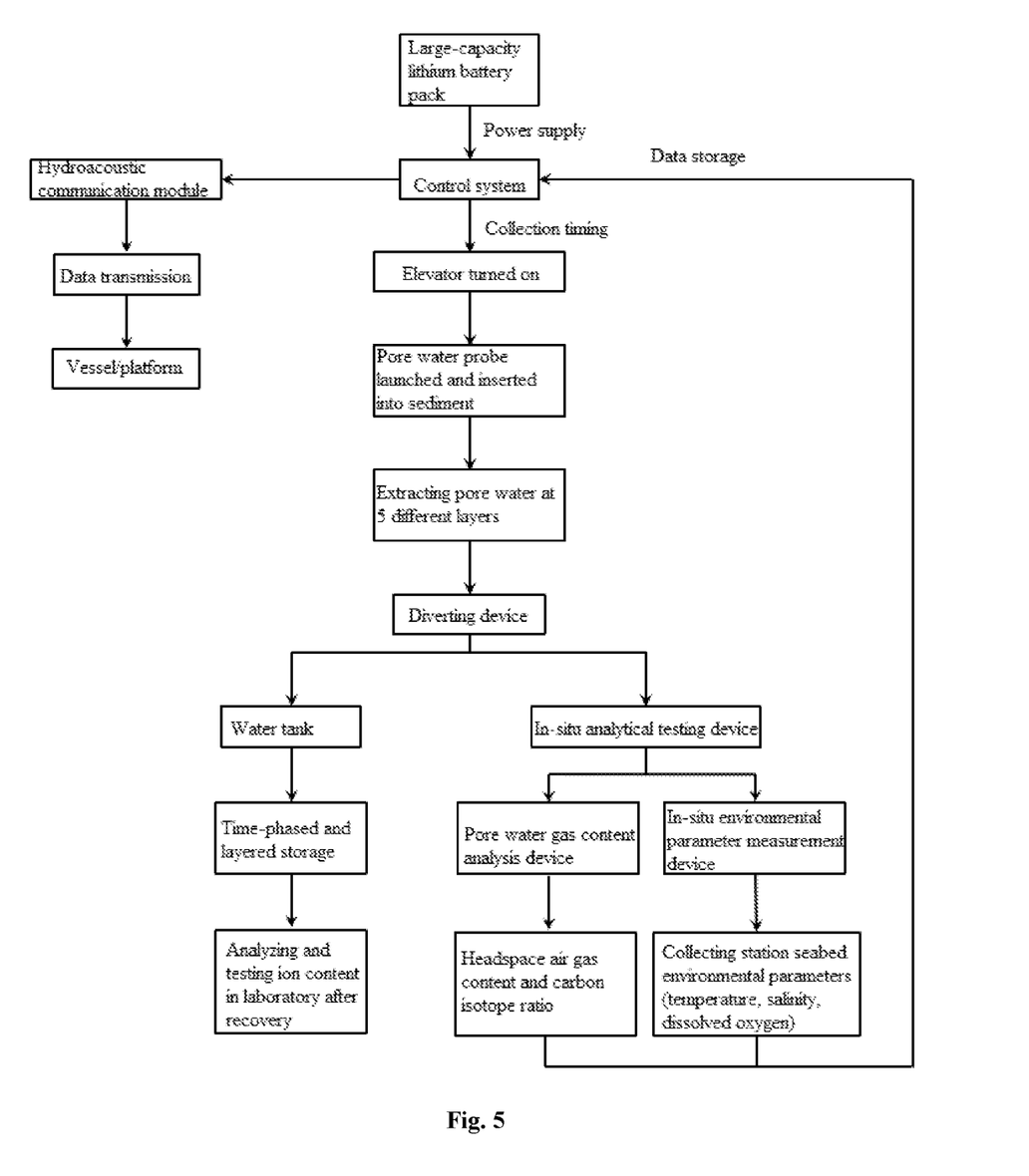
FIG. 5 is a flow chart showing the operation of the long-term in-situ sampling and analysis device for sediment pore water according to the present application.

As shown in FIG. 5, the working flow of the long-term in-situ sampling and analysis device for sediment pore water described in the present application is as follows.

The large-capacity lithium battery supplies power to the control system. The control system controls the elevator with the slide rail to start, so that the sediment pore water probe is lowered and inserted into the sediment on the seabed. The five parts of the probe respectively extract sediment pore water at five different layers. The extracted sediment pore water flows into the diverting device. On one hand, the diverting device distributes a portion of the sediment pore water to the first water storage tank, so that the purpose of time-phased and layered storage is achieved. The sediment pore water in the first water storage tank is used for laboratory analysis and testing of ion content. On the other hand, the diverting device distributes another portion of the sediment pore water to the in-situ analytical test device, including a dissolved gas of sediment pore water analysis device and an in-situ environment measurement device. The dissolved gas of sediment pore water analysis device is used to measure the gas content in the air and the carbon isotope ratio. The in-situ environment measurement device is used to collect seabed environmental parameters (including temperature, salinity, dissolved oxygen, etc.) of the station, and then store the measured data in the control system. Then the control system transmits the data to the vessel or platform through the hydroacoustic communication module for study.

The present application also provides a long-term in-situ sampling and analysis method for sediment pore water, including the following steps:

Step 1: Collection of sediment pore water, comprising inserting a probe into superficial sediment, and using a negative pressure method to extract the sediment pore water: starting up a peristaltic pump motor, forming a negative pressure in a second water storage device to cause a spring inside the second water storage device to be compressed, and forming a negative pressure by a spring force to extract the sediment pore water;

Step 2: Storage and analysis of sediment pore water, comprising assigning the sediment pore water acquired at different time periods from different sedimentary layers to the first water storage tank for pressure-keeping storage, and after a long-term in-situ sampling and analysis device for sediment pore water is recovered, analyzing and testing the stored sediment pore water in the laboratory to obtain the abnormality of $Cl^-$ and $SO_4^{2-}$ ions and its distribution characteristics;

Step 3: In-situ measurement of sediment pore water, comprising using a dissolved gas of sediment pore water analysis device to test in-situ $CH_4$ and $CO_2$ gas contents in the air at the top of the collected sediment pore water and the carbon isotope ratio in the gas; and using an in-situ environment measurement device to collect seabed environmental parameters of a sediment pore water collecting station, including temperature, salinity, pressure and dissolved oxygen, thereby providing basic environmental data for sediment pore water characterization;

Step 4: Underwater communication of data, comprising sending the collected data back through a hydroacoustic communication device to a survey vessel or platform on water surface for researchers to obtain data; and Step 5: Recovery of the long-term in-situ sampling and analysis device for sediment pore water, comprising during launching, causing the long-term in-situ sampling and analysis device for sediment pore water to sit on the seabed relying on an underwater negative buoyancy provided by the weight of a weight anchor block; during recovery, receiving by a releaser a recovery control signal sent by the survey vessel or platform on the water surface, and releasing the weight anchor block according to the recovery control signal; and after releasing the weight anchor block, completing the come-up and recovery of the long-term in-situ sampling and analysis device for sediment pore water using an underwater positive buoyancy provided by a buoyant material.

Therefore, the long-term in-situ sampling and analysis device for sediment pore water, according to the present application, can continuously collect sediment pore water in superficial sediments of the same station in the deep sea for a long period of time, store the sediment pore water in a time-phased and pressure-keeping manner for laboratory analysis after recovery, and measure geochemical information such as ion content in the sediment pore water; and at the same time, can perform rapid and in-situ analysis on the gas content characteristics in the sediment pore water and send the data back to the water surface through a hydroacoustic communication machine.

Finally, it should be noted that different time periods refer to that, for example, the long-term in-situ sampling and analysis device of sediment pore water is launched for collection once a month and each time collecting 5 layers of sediment pore water at the same time. During storage, the five layers of water in the first month are stored together (due to the small amount of sediment pore water, each of the first water storage tanks can be divided into five compartments, respectively storing sediment pore water of different layers), and the water in the second month is stored together, and so on, to achieve the storage of sediment pore water at different times.

Long-term continuous collection refers to that, for example, the long-term in-situ sampling and analysis device for sediment pore water is placed on the seabed for 6 months for collecting sediment pore water every other month. In this way, the sediment pore water at the same point on the seabed is collected sequentially. The continuous change of the sediment pore water content can be observed, and then the environmental changes in this period can be researched.

Various other changes and modifications may be made by those skilled in the art in light of the above-described technical solutions and concepts, and all such changes and modifications are intended to fall within the scope of the appended claims.

What is claimed is:

1. A long-term in-situ sampling and analysis device for sediment pore water, comprising a bracket, a probe, an elevator, a diverting device, a first water storage device, a second water storage device, a peristaltic pump, a dissolved gas of sediment pore water analysis device, and an in-situ environment measurement device, wherein the elevator is fixed to the bracket, the elevator is provided with a slide rail, the probe is connected with a slider, the probe is connected with the elevator by a cooperation of the slider and the slide rail, a motor is arranged at a top of the elevator, and the motor drives the slider to slide along a length of the slide rail by a drive assembly;

the diverting device is disposed above the probe and fixed to the bracket;

the first water storage device and the diverting device are connected by a first pipe;

the second water storage device is disposed at a top of the probe and connected to the probe through a second pipe;

the peristaltic pump is respectively connected to the second water storage device and the diverting device through a flexible connecting member; and the dissolved gas of sediment pore water analysis device and the in-situ environment measurement device are respectively connected to the diverting device through a third pipe.

2. The long-term in-situ sampling and analysis device for sediment pore water according to claim 1, further comprising a central control system, wherein the motor of the elevator, the peristaltic pump, the dissolved gas of sediment pore water analysis device and the in-situ environment measurement device are electrically connected to the central control system.

3. The long-term in-situ sampling and analysis device for sediment pore water according to claim 1, comprising a releaser, an anchor chain and a weight anchor block, wherein
   the releaser is disposed outside the bracket and fixed to the bracket;
   the weight anchor block is disposed under the releaser and detachably connected to the releaser through the anchor chain;
   an upper part of the bracket is wrapped with a buoyant material; and
   the releaser is configured to receive a recovery control signal sent by a survey vessel or platform located on water surface, and release the weight anchor block according to the recovery control signal.

4. The long-term in-situ sampling and analysis device for sediment pore water according to claim 1, further comprising a central control system and a hydroacoustic communication device, wherein the hydroacoustic communication device, the motor of the elevator, the peristaltic pump, the dissolved gas of sediment pore water analysis device, and the in-situ environment measurement device are electrically connected to the central control system; and
   the hydroacoustic communication device is configured to send data of the dissolved gas of sediment pore water analysis device and the in-situ environment measurement device to the survey vessel or platform.

5. The long-term in-situ sampling and analysis device for sediment pore water according to claim 1, wherein the first water storage device is composed of a plurality of first water storage tanks, and the plurality of first water storage tanks is distributed around a circumference of the diverting device; and the second water storage device is composed of a plurality of second water storage tanks, and the plurality of the second water storage tanks is respectively connected to the probe through the second pipe.

6. The long-term in-situ sampling and analysis device for sediment pore water according to claim 1, wherein the probe is composed of five parts, and the five parts respectively extract sediment pore water at five layers; and the second water storage device is composed of five second water storage tanks, and the five second water storage tanks are connected to the five parts of the probe by the second pipe, respectively.

7. The long-term in-situ sampling and analysis device for sediment pore water according to claim 1, further comprising a battery compartment, wherein the battery compartment is fixedly connected to the bracket.

8. A long-term in-situ sampling and analysis method for sediment pore water, comprising the following steps:
   1) collection of sediment pore water, comprising inserting a probe into superficial sediment, and using a negative pressure method to extract the sediment pore water, starting up a peristaltic pump motor, forming a negative pressure in a second water storage device to cause a spring inside the second water storage device to be compressed, and forming a negative pressure by a spring force to extract the sediment pore water;
   2) storage and analysis of sediment pore water, comprising distributing the sediment pore water acquired at different time periods from different sedimentary layers to a first water storage tank for pressure-keeping storage, and after a long-term in-situ sampling and analysis device is recovered, analyzing and testing the stored sediment pore water in a laboratory to obtain an abnormality of $Cl^-$ and $SO_4^{2-}$ ions and its distribution characteristics; and
   3) in-situ measurement of sediment pore water, comprising using a dissolved gas of sediment pore water analysis device to test in-situ $CH_4$ and $CO_2$ gas contents in the air at a top of the collected sediment pore water and a carbon isotope ratio in the gas; and using an in-situ environment measurement device to collect environmental parameters of a sediment pore water collecting station, including temperature, salinity, pressure and dissolved oxygen, thereby providing basic environmental data for sediment pore water characterization.

9. The long-term in-situ sampling and analysis method for sediment pore water according to claim 8, further comprising the following steps after step 3:
   4) underwater communication of data, comprising sending the collected data back through a hydroacoustic communication device to a survey vessel or platform on water surface for researchers to obtain data.

10. The long-term in-situ sampling and analysis method for sediment pore water according to claim 9, further comprising the following step after step 4):
   5) recovery of the long-term in-situ sampling and analysis device for sediment pore water, comprising during launching, causing the long-term in-situ sampling and analysis device for sediment pore water to sit on a seabed relying on an underwater negative buoyancy provided by the weight of a weight anchor block; during recovery, receiving by a releaser a recovery control signal sent by the survey vessel or platform on the water surface, and releasing the weight anchor block according to the recovery control signal; and after releasing the weight anchor block, completing come-up and recovery of the long-term in-situ sampling and analysis device for sediment pore water using an underwater positive buoyancy provided by a buoyant material.

* * * * *